United States Patent
Peloux et al.

(10) Patent No.: US 11,880,095 B2
(45) Date of Patent: Jan. 23, 2024

(54) OPTICAL DEVICE ADAPTED TO BE WORN BY A WEARER

(71) Applicant: Essilor International, Charenton-le-pont (FR)

(72) Inventors: Marius Peloux, Charenton-le-Pont (FR); Cecile Petignaud, Charenton-le-Pont (FR); Konogan Baranton, Charenton-le-Pont (FR); Benjamin Rousseau, Charenton-le-Pont (FR); Bruno Fermigier, Charenton-le-Pont (FR)

(73) Assignee: Essilor International, Charenton-le-pont (FR)

( * ) Notice: Subject to any disclaimer, the term of this patent is extended or adjusted under 35 U.S.C. 154(b) by 956 days.

(21) Appl. No.: 16/605,036

(22) PCT Filed: Apr. 19, 2018

(86) PCT No.: PCT/EP2018/060101
§ 371 (c)(1),
(2) Date: Oct. 14, 2019

(87) PCT Pub. No.: WO2018/193057
PCT Pub. Date: Oct. 25, 2018

(65) Prior Publication Data
US 2021/0132414 A1    May 6, 2021

(30) Foreign Application Priority Data

Apr. 20, 2017 (EP) .................................. 17305457

(51) Int. Cl.
*G02C 7/08* (2006.01)
*G02B 27/00* (2006.01)
(Continued)

(52) U.S. Cl.
CPC ............. *G02C 7/083* (2013.01); *A61B 3/113* (2013.01); *G02B 27/0093* (2013.01); *G02C 11/10* (2013.01); *G02C 2202/20* (2013.01)

(58) Field of Classification Search
CPC ........ G02C 7/081–085; G02C 2202/20; A61B 3/113; G02B 3/14; G02B 27/0093
See application file for complete search history.

(56) References Cited

U.S. PATENT DOCUMENTS 5,229,885 A * 7/1993 Quaglia ................. G02C 7/085
351/158
5,359,444 A * 10/1994 Piosenka ................. G02B 7/32
349/13
(Continued)

FOREIGN PATENT DOCUMENTS

DE   102015214671 A1 *  2/2017  ............. A61B 3/103
EP   2 693 260 A      2/2014
(Continued)

OTHER PUBLICATIONS

English machine translation of DE-102015214671-A1 (Year: 2015).*
(Continued)

*Primary Examiner* — Nicholas R. Pasko
(74) *Attorney, Agent, or Firm* — Oblon, McClelland, Maier & Neustadt, L.L.P.

(57) ABSTRACT

An optical device including an active programmable lens having an adjustable optical power depending on a prescription of a wearer and being relative to a vision distance and/or direction of an eye of the wearer, a vision sensor adapted to measure vision data relating to the vision distance and/or direction of the eye, and an optical power controller that includes a memory storing computer executable instructions and adapted to store measured vision data and two predetermined optical power states corresponding to an optical power relative to a range of vision distance and/or direction (Continued)

of the eye, and a processor for executing the stored computer executable instructions, which include instructions for adjusting the adjustable optical power between the predetermined optical power states with a resolution smaller than or equal to 0.25 D when the vision data passes from one range of vision distance and/or direction to another.

17 Claims, 2 Drawing Sheets

(51) Int. Cl.
*G02C 11/00* (2006.01)
*A61B 3/113* (2006.01)

(56) References Cited

U.S. PATENT DOCUMENTS

| | | | |
|---|---|---|---|
| 6,517,203 B1 | 2/2003 | Blum et al. | |
| 7,264,354 B2* | 9/2007 | Blum | A61B 3/04 351/216 |
| 11,567,349 B2* | 1/2023 | Baranton | G02C 7/083 |
| 2004/0156021 A1 | 8/2004 | Blum et al. | |
| 2005/0036109 A1 | 2/2005 | Blum et al. | |
| 2005/0237485 A1 | 10/2005 | Blum et al. | |
| 2007/0216864 A1 | 9/2007 | Blum et al. | |
| 2007/0242224 A1 | 10/2007 | Blum et al. | |
| 2008/0024718 A1 | 1/2008 | Blum et al. | |
| 2008/0174732 A1 | 7/2008 | Blum et al. | |
| 2008/0208335 A1* | 8/2008 | Blum | G02C 7/049 623/6.22 |
| 2008/0239236 A1 | 10/2008 | Blum et al. | |
| 2008/0246922 A1 | 10/2008 | Blum et al. | |
| 2011/0043925 A1 | 2/2011 | Chavel et al. | |
| 2011/0285959 A1* | 11/2011 | Gupta | G02C 7/083 351/159.01 |
| 2012/0019773 A1* | 1/2012 | Blum | G02B 3/14 351/159.01 |
| 2013/0176537 A1* | 7/2013 | Thompson | A61B 3/032 351/239 |
| 2013/0201447 A1* | 8/2013 | Thompson | A61B 3/1015 351/201 |
| 2014/0218647 A1* | 8/2014 | Blum | B29D 11/00009 349/13 |
| 2014/0347623 A1* | 11/2014 | Inoue | G02B 27/0093 351/159.41 |
| 2015/0185504 A1 | 7/2015 | Peloux | |
| 2017/0059886 A1 | 3/2017 | Fayolle et al. | |
| 2017/0160440 A1 | 6/2017 | Yadin et al. | |
| 2018/0017812 A1 | 1/2018 | Peloux | |
| 2020/0018991 A1* | 1/2020 | Baranton | G02C 7/083 |

FOREIGN PATENT DOCUMENTS

| | | | |
|---|---|---|---|
| WO | WO-2014179857 A1 * | 11/2014 | A61B 3/113 |
| WO | WO 2015/186010 A1 | 12/2015 | |

OTHER PUBLICATIONS

Lin et al., "Electrically tunable-focusing and polarizer-free liquid crystal lenses for ophthalmic applications," Optics Express, vol. 28, No. 8, Apr. 22, 2013, 9428-9436, DOI:10.1364/OE.21.009428. (Year: 2013).*
International Search Report dated Jun. 5, 2018 in PCT/EP2018/060101 filed on Apr. 19, 2018.

* cited by examiner

OPTICAL DEVICE ADAPTED TO BE WORN BY A WEARER

FIELD OF THE INVENTION

The invention relates to an optical device adapted to be worn by a wearer comprising an active programmable lens, a vision sensor and an optical power controller.

BACKGROUND OF THE INVENTION

Usually, an active lens permits a variation of the optical power of the lens while being worn by a wearer.

It exists active Fresnel lenses, pixelized lenses, Alvarez lenses or fluidic lenses, in which the optical power is adjusted according to the wearer's needs, for instance for compensating the lack of accommodation of long-sighted wearers.

Plus, it exists Fresnel lenses, with liquid crystal technology, which are activated when the wearer lows his head.

Such active lenses are integrated in a frame which comprises a gaze-direction sensor, such as an eye-tracker or a camera, for measuring data in order to adjust the optical power based on such measured data. The frame further comprises a battery for supplying the active lenses and the gaze-direction sensor.

However, due to the power consumption of the adjustment of the optical power, the battery are heavy and large.

Moreover, in general, the optical devices for adjusting the optical power in real time are complex. Indeed, such optical devices need to comprise gaze-direction sensors that continuously and quickly measure the gaze-direction of the eyes of the wearer.

Plus, such optical devices need active lenses capable of quickly adjusting the optical power. Hence, such optical devices are expensive.

Furthermore, in such optical device, the wearer may perceive the variations of optical power of the active lenses.

With such an optical device, the wearer may feel discomfort.

For instance, if the wearer fixes an object and slightly moves his head, his vision distance and the vision direction of the eye of the wearer on the optical device change. If the optical power of the active lens changes permanently, then the active lens will cause a magnification effect, when approaching, or a continuous reduction, when moving away, which can be perceived unpleasantly for the wearer as if the object viewed by the wearer was in motion.

If the wearer fixes a moving target, for which the position in the visual field changes, and the prismatic power of the active lens changes continuously, then the wearer will perceive distortions of the environment which will vary dynamically, and which will disturb the wearer.

Moreover, with Alvarez lenses, which are motorized active lenses, the active lenses consume power only when the optical power need to be adjusted. Thus, if the optical power is permanently modified, the power consumed by the active lenses is increased. Plus, such lenses are slow, and that it is therefore difficult to have the optical power varying without latency. This can be perceived as a visual discomfort of the wearer, as it takes more time to accommodate in order to have a clear image.

Plus, an optical device using a "time of flight" type detector consumes power in particular when it emits light, infrared light, to illuminate the scene located in front of the wearer. Moreover, an eye-tracker consumes power when it illuminates the eyes of the wearer, with infrared light.

Thus, there is a need for an optical device adapted to be worn by a wearer for adjusting the optical power of the optical device while the optical device is worn by the wearer which require components without constraints of precision and/or speed.

More precisely, there is a need for an optical device all the time adapted to the wearer's needs, which is less complex, expensive and heavy than the optical devices according to the prior art.

One object of the invention is to provide such an optical device.

SUMMARY OF THE INVENTION

To this end, the invention proposes an optical device adapted to be worn by a wearer, the wearer having a prescription for at least one eye, the optical device comprising at least:
- an active programmable lens having an adjustable optical power and extending between at least one eye of the wearer and the real world scene when the optical device is worn by the wearer, the adjustable optical power depending on the prescription of said at least one eye of the wearer and being relative to a vision distance and/or a vision direction of said at least one eye of the wearer,
- a vision sensor adapted to measure vision data relating to the vision distance and/or vision direction of said at least one eye of the wearer using the optical device, and
- an optical power controller comprising:
   - a memory storing at least computer executable instructions and adapted to store vision data measured by the vision sensor and at least two predetermined optical power states, each predetermined optical power state corresponding to an optical power relative to a range of vision distance and/or vision direction of said at least one eye of the wearer; and
   - a processor for executing the stored computer executable instructions so as to control the adjustable optical power of the active programmable lens, wherein the computer executable instructions comprise instructions for adjusting the adjustable optical power of the active programmable lens from one predetermined optical power state to the other when the vision data indicate a vision distance and/or vision direction passing from the range of distance and/or direction of one predetermined optical power state to another, the adjustment resolution of the adjustable optical power of the active programmable lens being smaller than or equal to 0.25 D.

Advantageously, the optical device according to the invention allows a variation of the optical power while the optical device is worn by the wearer.

Moreover, the optical device according to the invention allows a higher comfort for the wearer. More precisely, adjusting the adjustable optical power of the active programmable lens based on a function comprising different steps, for instance a first predetermined optical power state and a second predetermined optical power state, allows avoiding a visual discomfort of the wearer, while reducing the power consumption of the optical device.

According to embodiments, the optical device according to the invention may further comprise one or several of the following features according to any possible combination:
- the adjustment resolution of the adjustable optical power of the active programmable lens is smaller than or equal to 0.12 D;

the difference between the at least two predetermined optical power states is greater than or equal to the adjustment resolution of the adjustable optical power of the active programmable lens;

the difference of optical power between the at least two predetermined optical power states depends on the prescription of said at least one eye of the wearer;

the prescription of said at least one eye of the wearer comprises power addition;

the vision data comprises an indication of the eye accommodation need of the wearer;

the adjustable optical power is a spherical optical power;

the vision sensor is adapted to measure a vision direction of said at least one eye of the wearer and wherein the computer executable instructions comprise instructions for adjusting the optical function, for example the optical power and/or the optical center, of the active programmable lens based on the vision direction of said at least one eye of the wearer;

the computer executable instructions comprise instructions for moving the optical function and/or the optical center of the active programmable lens with the vision direction of said at least one eye of the wearer;

the vision data comprises an indication of the prism tolerance of the wearer;

the computer executable instructions comprise instructions for adjusting the prism of the active programmable lens;

the memory is adapted to store a plurality of predetermined optical power states, each predetermined optical power state corresponding to an optical power relative to a range of vision distance and/or vision direction of said at least one eye of the wearer;

the active programmable lens is a Fresnel lens and wherein the computer executable instructions comprise instructions for adjusting the at least one prismatic optical power from one predetermined optical power state to another so as to move the central ring upon the vision direction of said at least one eye of the wearer;

the at least two predetermined optical power states comprise a non-uniform and progressive spherical optical power distribution, and wherein the geometrical variation of optical power of the active programmable lens is smaller than or equal to 1 D;

the optical device comprises at least two active programmable optical lenses having adjustable optical powers and extending respectively between the right and left eyes of the wearer and the real world scene when the optical device is worn by the wearer, and the computer executable instructions comprise instructions for adjusting the optical power of both active programmable lenses;

the vision data comprises an indication of the difference of prism tolerance of the wearer between the right and left eyes of the wearer;

the vision sensor is adapted to measure the vision direction of both eyes of the wearer;

the computer executable instructions comprise instructions for adjusting the prisms of both active programmable lenses independently one from the other;

the adjustment resolution of the adjustable optical power of the active programmable lens (20) is larger than or equal to 0.1 D.

BRIEF DESCRIPTION OF THE DRAWINGS

Other characteristics and advantages of the invention will become more apparent from the claims and from the following description of some embodiments given by way of example without limitation with reference to the drawings:

Elements in the figures are illustrated for simplicity and clarity and have not necessarily been drawn to scale. For example, the dimensions of some of the elements in the figures may be exaggerated relative to other elements to help improve the understanding of the embodiments of the present invention.

DETAILED DESCRIPTION OF PREFERRED EMBODIMENTS

Figure 1:
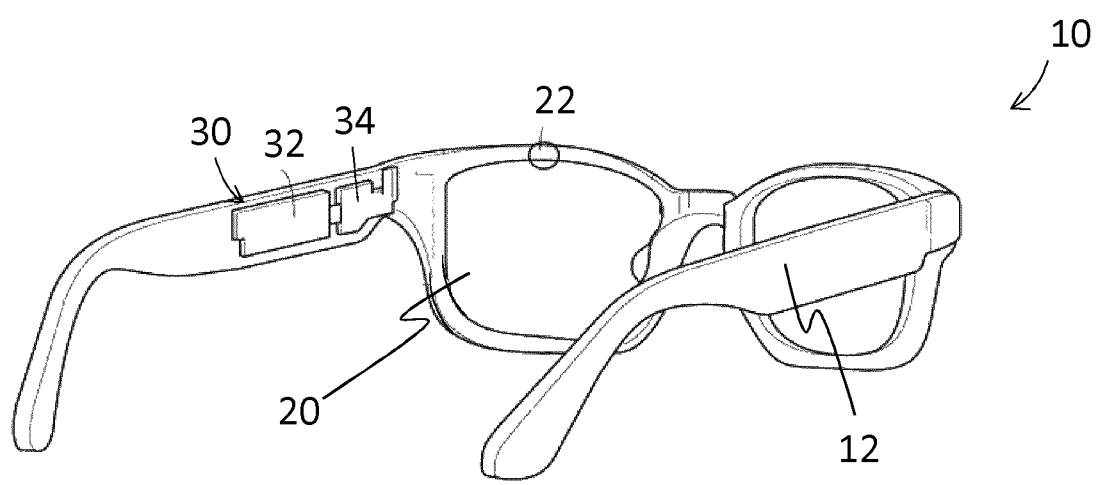
FIG. 1 is an optical device according to the invention.

The invention relates to an optical device adapted to be worn by a wearer. The wearer has a prescription for at least one eye. The optical device 10 may be a head-mounted device, as represented in FIG. 1, comprising a frame 12.

The optical device 10 comprises at least one, for instance two, active programmable lens 20. The programmable lens 20 is configured to extend between at least one eye of the wearer and the real world scene when the optical device is worn by the wearer. The programmable lens 20 may be an optical lens, an ophthalmic lens, a spectacle lens, a progressive or a single vision lens.

The active programmable lens 20 has an adjustable optical power. The adjustable optical power depends on the prescription of the eye of the wearer. The adjustable optical power is relative to a vision distance and/or a vision direction of the eye of the wearer.

The optical device 10 comprises a vision sensor 22. The vision sensor 22 is adapted to measure vision data relating to the vision distance and/or vision direction of the eye of the wearer using the optical device 10.

The vision sensor may measure a vision distance and/or a vision direction of the eye of the wearer at a low frequency for instance every 1 s, or every 0.5 s. The vision sensor may measure a vision distance and/or a vision direction of the eye of the wearer with low accuracy, for example by measuring a proximity corresponding to 0.1 D or 0.2 D. The vision sensor may be an eye-tracker measuring a low accurate vision direction, for example of precision in the order of the size of the optical function, for instance of the size of a Fresnel ring.

The optical device 10 comprises an optical power controller 30. The optical power controller 30 comprises a memory 32 and a processor 34.

The memory 32 is configured to store computer executable instructions. The memory 32 may also be configured to store data received by the optical power controller 30. The memory 32 is adapted to store vision data measured by the vision sensor. The memory 32 is adapted to store at least two predetermined optical power states. A predetermined optical power state corresponds to an optical power relative to a range of vision distance and/or vision direction of an eye of the wearer.

The memory may be adapted to store a plurality of predetermined optical power states. Each predetermined optical power state of the plurality of predetermined optical power states corresponds to an optical power relative to a range of vision distance and/or vision direction of the eye of the wearer.

The processor 34 is configured to execute the stored computer executable instructions so as to control the optical power of the active programmable lens 20.

The computer executable instructions comprise instructions for adjusting the adjustable optical power of the active programmable lens 20 from one predetermined optical power state to the other when the vision data indicate a vision distance and/or vision direction passing from the range of distance and/or direction of one predetermined optical power state to another. The adjustment resolution of the adjustable optical power of the active programmable lens 20 is smaller than or equal to 0.25 D. The adjustment resolution of the adjustable optical power of the active programmable lens 20 is preferably smaller than or equal to 0.12 D.

Advantageously, such adjustment resolution of the adjustable optical power of the active programmable lens allows a higher comfort for the wearer.

The adjustment of the optical power may be applied on a part of the field of view of the wearer or in the whole field of view of the wearer. In other words, the adjustment of the optical power may be applied on a part of the active programmable lens, or on the whole active programmable lens. For instance, the optical power may remain constant in the part of the lens used for central vision of the wearer and may be adjusted in the part of the lens used for peripheral vision of the wearer.

The adjustable optical power of the active programmable lens may be a function depending on the vision distance and/or vision direction of the eye of the wearer.

The adjustable optical power of the active programmable lens may be a function by steps, for instance defined by the following equation:

$$\begin{cases} \text{for } 0 \le \frac{1}{d} < \Delta P, P_{target} = \frac{1}{d} \\ \text{for } \Delta P \le \frac{1}{d}, P_{target} = \Delta P \end{cases} \quad (1)$$

where $P_{target}$ is the adjustable optical power adapted to a vision distance d measured by the vision sensor and $\Delta P$ is the addition of the active programmable lens of the eye of the wearer.

The adjustable optical power of the active programmable lens may be determined based on physiological tests on the wearer, for instance with an optical device comprising a frame, lenses with adjustable optical power, and a vision sensor adapted for measuring a vision distance of the wearer. The wearer may indicate, for two different vision distance, which value of optical power is more comfortable, so that the wearer can observe a scene without accommodation or with the less accommodation possible.

For evaluating the addition necessary for the eye of the wearer, the wearer may be asked to read the smallest possible characters. The test is placed, for example at 40 cm of the eyes of the wearer, and convex lenses are progressively introduced, by 0.25 D, until the wearer can read the smallest text. The maximum amplitude of accommodation is equal to: 2.50 D, with the convex power added. Once the amplitude of accommodation is measured, the addition is calculated so that the wearer uses the two-thirds (Percival's criterion) or a half (Sheard's criterion) of his remaining accommodation amplitude. The addition is equal to the inverse of the reading distance minus the two-thirds or the half of the maximum amplitude of accommodation. The comfort of vision of the wearer of this addition to the usual distance of reading of the wearer is checked.

The adjustable optical power of the active programmable lens may be evaluated based on the average of the adjustable optical powers obtained for a significant number of wearers.

The adjustable optical power of the active programmable lens may be standardized, depending on the age of the wearer, and/or on the addition needed, and/or on possible ocular pathologies, such as early cataracts or photophobia, and/or on the luminosity of the environment, and/or on the activity of the wearer, such as reading or playing sports.

The adjustable optical power of the active programmable lens may be personalized for each wearer.

The adjustable optical power of the active programmable lens may be customizable a posteriori. For instance, when the wearer receives the optical device, it contains a default function defining the adjustment of the adjustable optical power of the active programmable lens, and the wearer may adjust the adjustable optical power of the active programmable lens by means of a software.

The predetermined optical power states may be determined by the wearer. For instance, the wearer may adjust the predetermined optical power states to have the optical power of the active lens greater than or smaller than the initial value of optical power.

The adjustable optical power of the active programmable lens may be a function by steps defined by the equation (1), with $\Delta P=1.5$ D.

For instance, by considering a non-presbyopic, corrected emmetropic or ametropic wearer may see clearly over a range of distance d between 25 cm and the infinity, the distance d equal to 25 cm requiring 4 D of accommodation and the distance d equal to the infinite requiring 0 D, namely no effort of accommodation is needed.

Figure 2:
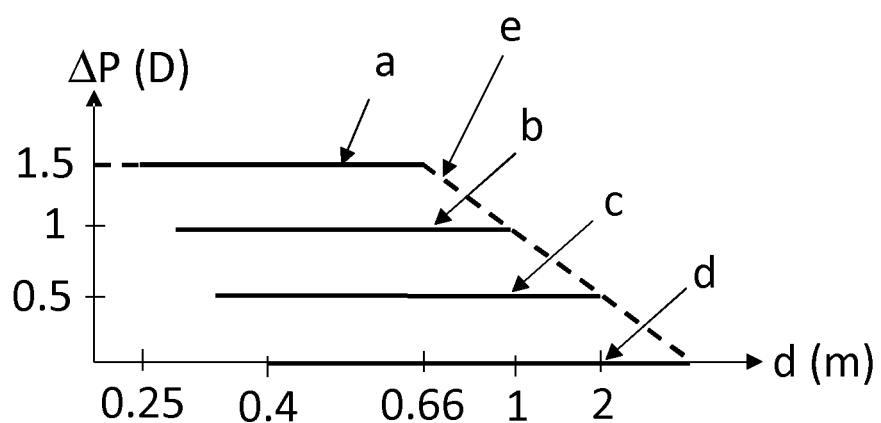
FIGS. 2 and 3 are graphs representing predetermined optical power states corresponding to an adjustable optical power of an active programmable lens relative to a range of vision distance of an eye of a wearer.

For instance, by considering a presbyopic wearer, the function of the addition depending on the vision distance of the eye of the wearer is represented in FIG. 2.

The wearer may see clearly over a range of distance d between 40 cm and the infinity (curve a), with a maximum accommodation when viewing at a distance of 40 cm. The wearer feels more comfort when looking at the infinite than when looking at a distance of vision d equal to 40 cm.

When adding an optical power on the lens of the wearer, for instance 0.5 D, the wearer may see clearly over a range of distance d between around 33 cm and 2 m (curve b). The wearer feels more comfort when looking at a distance of vision d equal to 2 m than when looking at a distance of vision d equal to around 33 cm.

When adding an optical power on the lens of the wearer, for instance 1 D, the wearer may see clearly over a range of distance d between around 28 cm and 1 m (curve c). The wearer feels more comfort when looking at a distance of vision d equal to 1 m than when looking at a distance of vision d equal to around 28 cm.

When adding an optical power on the lens of the wearer, for instance 1.5 D, the wearer may see clearly over a range of distance d between 25 cm and around 66 cm (curve d). The wearer feels more comfort when looking at a distance of vision d equal to around 66 cm than when looking at a distance of vision d equal to 25 cm.

The adjustable optical power of the active programmable lens considered may be a function linking the more comfortable points of vision of the wearer (curve e).

Figure 3:
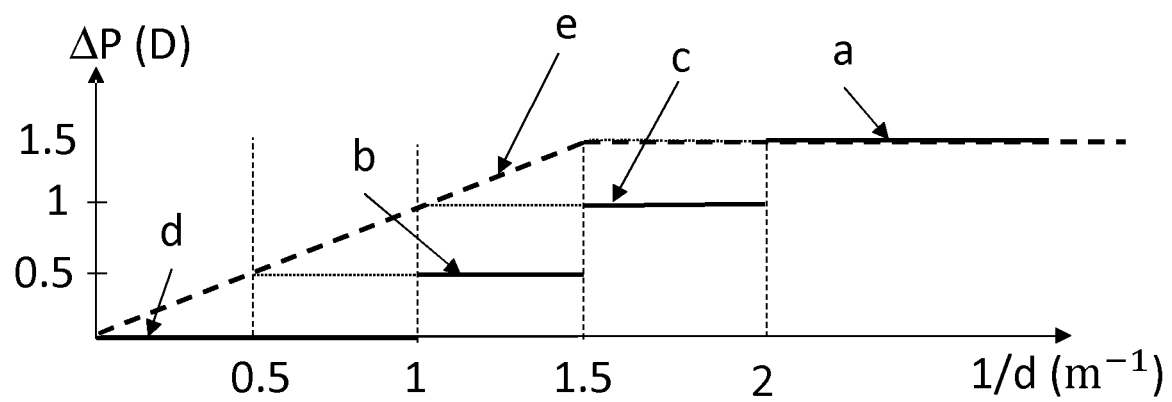

With reference to FIG. 3, four predetermined optical power states are represented. Of course, more than or fewer than four predetermined optical power states may be implemented in the processor.

The predetermined power states may operate in hysteresis (curves represented with dots).

In FIG. 3, the first predetermined power state (curve d) corresponds to an optical power equal to 0 D relative to a range of the inverse of vision distance of an eye of the wearer comprised between 0 m$^{-1}$ and 1 m$^{-1}$, when operating in hysteresis or not.

The second predetermined power state corresponds to an optical power equal to 0.5 D relative to a range of the inverse of vision distance of an eye of the wearer comprised between around 1 m$^{-1}$ and 1.5 m$^{-1}$. When operating in hysteresis, the second predetermined power state corresponds to an optical power equal to 0.5 D relative to a range of the inverse of vision distance of an eye of the wearer s comprised between 0.5 m$^{-1}$ and 1.5 m$^{-1}$.

The third predetermined power state corresponds to an optical power equal to 1 D relative to a range of the inverse of vision distance of an eye of the wearer s comprised between 1.5 m$^{-1}$ and 2 m$^{-1}$. When operating in hysteresis, the third predetermined power state corresponds to an optical power equal to 1 D relative to a range of the inverse of vision distance of an eye of the wearer s comprised between 1 m$^{-1}$ and 2 m$^{-1}$.

The fourth predetermined power state corresponds to an optical power equal to 1.5 D relative to a range of the inverse of vision distance of an eye of the wearer s comprised between 2 m$^{-1}$ and the infinite. When operating in hysteresis, the fourth predetermined power state corresponds to an optical power equal to 1.5 D relative to a range of the inverse of vision distance of an eye of the wearer s comprised between 1.5 m$^{-1}$ and the infinite.

Considering, for example, the second predetermined power state as a starting condition. The value of the adjustable optical power is 0.5 D, with a range of the inverse of vision distance between 0.5 m$^{-1}$ and 1.5 m$^{-1}$.

The adjustable optical power remains constant as long as the vision distance from the eye, which is continuously measured, is not out of the range of the vision distance corresponding to the second predetermined optical power state for a duration at least equal to a predetermined period of time, for instance 1 second.

When the measured vision distance from the eye is out of the range of the vision distance corresponding to the second predetermined optical power state for a duration equal to the predetermined period of time, the vision sensor informs the processor of the last vision distance value d measured.

The processor determines the range of vision distance corresponding to the measured vision distance d, in order to determine the corresponding predetermined optical power state.

The processor adjusts the optical power of the lens from the second predetermined optical power state to the predetermined optical power state corresponding to the range of vision distance having the measured vision distance d.

The optical device returns to standby and the steps are repeated.

By operating in hysteresis, the optical device avoids the flickering.

Indeed, if only the range of vision distance corresponding to the predetermined power state without hysteresis were considered, if for example, for a value of optical power equal to 0.5 D, a vision distance equal to 1.6 m were measured for a duration greater than 1 s, the value of the optical power then becomes equal to 1 D. If the measured vision distance by the vision sensor oscillates around this value of vision distance equal to 1.6 m, close to the boundary between two consecutive predetermined optical power states, it would lead to the oscillation of the value of the optical power between 0.5 D and 1 D.

The measuring frequency of the vision distance may advantageously be greater than the inverse of the predetermined period of time in order to minimize the power consumption of the optical device. The measuring frequency of the vision distance may be the lowest possible frequency.

In order to refine the choice of the values of predetermined optical power stages, a merit function to be minimized may be defined. Such merit function may depend on the values of optical powers of the predetermined optical power stages or of the range of vision distance and/or vision direction of the predetermined optical power stages. For instance, the merit function may depend on the average number of optical power adjustment per minute of the active programmable lens, which indicates the optical device consumption, and the average optical power deviation of the active programmable lens relative to a predetermined target function. These criteria may be evaluated on a series of scenarios representative of everyday life, which may be recorded from optical devices worn by test wearers, equipped with vision sensors.

The difference between the two predetermined optical power states may be greater than or equal to the adjustment resolution of the adjustable optical power of the active programmable lens 20.

The difference of optical power between the at least two predetermined optical power states may depend on the prescription of the eye of the wearer.

The prescription of the eye of the wearer may comprise power addition.

The vision data may comprise an indication of the eye accommodation need of the wearer.

The adjustable optical power may be a spherical optical power. The adjustment of the spherical optical power allows limiting the eye accommodation.

The vision sensor 22 may be adapted to measure a vision direction of the eye of the wearer.

The computer executable instructions may comprise instructions for adjusting the optical function of the active programmable lens 20 based on the vision direction of the eye of the wearer. The computer executable instructions may comprise instructions for adjusting the optical power and/or the optical center of the active programmable lens 20 based on the vision direction of the eye of the wearer.

The optical function may comprise the dioptric function, the light absorption, the polarizing capability or the reinforcement of contrast capacity.

The dioptric function corresponds to the programmable lens power, for instance the mean power or the astigmatism, as a function of the gaze direction.

The optical function of the optical device may comprise a sun protection function, for example by controlling a transmission parameter of the programmable lens or the polarization of a surface of the programmable lens.

The computer executable instructions may comprise instructions for moving the optical function and/or the optical center of the active programmable lens 20 with the vision direction of the eye of the wearer. In other words, the optical center of the active programmable lens 20 may be adjusted in position by moving the optical function and/or the optical center of the active programmable lens 20 with the vision direction of the eye of the wearer.

The presence of steps in position allows reducing the dynamic variations of the distortions due to prismatic effects. Indeed, the position of the optical center remains constant as long as the adjustable optical power of the active programmable lens is not adjusted from one predetermined optical power state to another.

For instance, when the wearer is looking in a zone of the active programmable lens too far from the center of the optical function of the active programmable lens, his visual acuity is reduced. The optical center of the active programmable lens 20 may be moved with the vision direction of the eye of the wearer, so as to center the optical function on the vision direction.

For example, for a well-corrected wearer, the optical function may be refocused when the visual acuity decreases under a predetermined value. A decrease in visual acuity may be, for example, linked to aberrations present at the edges or at the periphery of the optical function. The aberrations may be aberrations of the type of spherical power, cylindrical power, higher order optical aberration, diffusion defects or cosmetic defects.

For example, the optical function may be refocused by considering that the quality of the image relative to the diffractive behavior of the optical device is deteriorated with the distance to the optical axis. For a Fresnel lens having Fresnel rings to provide a large field of view, when the vision direction of the eye of the wearer for the central vision remains in the area of one Fresnel ring, the N Fresnel ring, the position of the optical function may be maintained. The position of the optical function may be refocused when the vision direction of the eye of the wearer for the central vision approaches or exceeds the N Fresnel ring, because the optical quality is degraded when moving away from the central ring.

The computer executable instructions may comprise instructions for adjusting the optical power and/or the position of the optical function of the active programmable lens 20 with the vision direction of the eye of the wearer with a temporal step. In other words, the optical power and/or the position of the optical function of the active programmable lens 20 may be adjusted continuously with a temporal step, for instance greater than an ocular saccade and around few seconds.

For example, the position of the optical function, where the optical power may be continuous, for example, based on the equation (1), may be adjusted. The optical power remains constant over a minimum period of time, for example over 0.5 s. The adjustable optical power is re-evaluated at this time, depending, for example, on the average of the vision distances between the two periods of time. The succession of optical powers are constant between two periods of time. Passing from one optical power to another may be done, for example, instantaneously, or at least at the speed of the optical device.

The adjustable optical power of the active programmable lens may be adjusted during an eye-blink, or during an ocular saccade, so that some abrupt changes are not perceived by the wearer.

For instance, the wearer is looking through a first area of the active programmable lens, and while exploring the environment, the wearer have an ocular saccade during which his vision direction is moved toward a second area of the lens, for example distant from the first area. The vision sensor is not able to measure this phenomenon, which is too fast to be measured. When the wearer's vision direction stays long enough in the second area, for instance 0.5 s or more, the vision direction of the wearer may be measured and the active programmable lens may adjust the optical power in at least one position of the active programmable lens during the next eye-blink or the ocular saccade.

The adjustable optical function may be adjusted at a low speed, below a perception threshold of the wearer, for instance below at 0.1 D/s.

The predetermined optical power states may be modified according to the activity of the wearer. For example, under reading conditions, the function of the active programmable lens may stay stable so as to not disturb the programming of the ocular saccades. Moreover, a blur is not inconvenient under normal conditions of reading, since it is even recurrent because of a lag of accommodation, corresponding to a residual defect of the eye when focusing.

When the wearer is moving, the optical function of the active programmable lens may be adjusted quickly, especially in the vision direction from the near vision to the far vision.

The vision data may comprise an indication of the prism tolerance of the wearer. The prism tolerance of the wearer corresponds to the tolerance of the wearer such that the wearer does not perceive the deviations of prism.

The computer executable instructions may comprise instructions for adjusting the prism of the active programmable lens 20.

The vertical prism of the active programmable lens 20 may be adjusted. Similarly, the horizontal prism of the active programmable lens 20 may be adjusted.

The active programmable lens may be a Fresnel lens. More precisely, the active programmable lens 20 may be pixelized so as to form a Fresnel lens.

The computer executable instructions may comprise instructions for adjusting the at least one prismatic optical power from one predetermined optical power state to another so as to move the central ring of the Fresnel lens upon the vision direction of the eye of the wearer.

The predetermined optical power states may comprise a non-uniform and progressive spherical optical power distribution.

The geometrical variation of optical power of the active programmable lens 20 may be smaller than or equal to 1 D.

The optical device 10 may comprise two active programmable lenses 20. Each active programmable lens has an adjustable optical power.

An active programmable lens 20 extends between the right eye of the wearer and the real world scene when the optical device is worn by the wearer. The other active programmable lens 20 extends between the left eye of the wearer and the real world scene when the optical device is worn by the wearer.

The computer executable instructions may comprise instructions for adjusting the optical power of both active programmable lenses 20.

The computer executable instructions may comprise instructions for adjusting the optical powers of both active programmable lenses 20 independently one from the other. For instance, if the wearer have different corrections for the right and left eyes, it may be advantageous to adjust the optical power of only one of the active programmable lens, or to adjust the optical power of the active programmable lenses independently one from the other. Moreover, only one of the optical power of the programmable lenses may need to be adjusted. Plus, the right and left eyes of the wearer may have different sensitivities, and thus a different adjustment of the optical power may be needed for the right and left eyes. The programmable lenses may be adjusted at the same time or at different moments, according to the wearer's needs.

The vision data may comprise an indication of the difference of prism tolerance of the wearer between the right and left eyes of the wearer.

The vision sensor 22 may be adapted to measure the vision direction of both eyes of the wearer.

The computer executable instructions may comprise instructions for adjusting the prisms of both active programmable lenses independently one from the other.

The invention has been described above with the aid of embodiments without limitation of the general inventive concept. Moreover, the embodiments of the invention may be combined without any restriction.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference

The invention claimed is:

1. An optical device adapted to be worn by a wearer, the wearer having a prescription for at least one eye, the optical device comprising:
   an active programmable lens having an adjustable optical power and extending between at least one eye of the wearer and a real world scene when the optical device is worn by the wearer, the adjustable optical power depending on the prescription of said at least one eye of the wearer and being relative to a vision distance and/or a vision direction of said at least one eye of the wearer;
   a vision sensor adapted to measure vision data relating to the vision distance and/or vision direction of said at least one eye of the wearer using the optical device; and
   an optical power controller comprising:
      a memory storing at least computer executable instructions and adapted to store vision data measured by the vision sensor and at least two predetermined optical power states, each predetermined optical power state corresponding to an optical power relative to a range of vision distance and/or vision direction of said at least one eye of the wearer, and
      a processor for executing the stored computer executable instructions so as to control the adjustable optical power of the active programmable lens,
   wherein the computer executable instructions comprise instructions for adjusting the adjustable optical power of the active programmable lens from one predetermined optical power state to the other when the vision data indicate a vision distance and/or vision direction passing from the range of vision distance and/or vision direction of one predetermined optical power state to another, an adjustment resolution of the adjustable optical power of the active programmable lens being smaller than or equal to 0.25 D,
   wherein the vision data comprises an indication of prism tolerance of the wearer, and
   wherein the prism tolerance of the wearer corresponds to a range of prismatic power specific to the wearer, such that the wearer does not perceive deviations of a prism.

2. The optical device according to claim 1, wherein the adjustment resolution of the adjustable optical power of the active programmable lens is smaller than or equal to 0.12 D.

3. The optical device according to claim 1, wherein a difference between the at least two predetermined optical power states is greater than or equal to the adjustment resolution of the adjustable optical power of the active programmable lens.

4. The optical device according to claim 1, wherein a difference of optical power between the at least two predetermined optical power states depends on the prescription of said at least one eye of the wearer.

5. The optical device according to claim 1, wherein the prescription of said at least one eye of the wearer comprises power addition.

6. The optical device according to claim 1, wherein the vision data comprises an indication of eye accommodation need of the wearer.

7. The optical device according to claim 1, wherein the adjustable optical power is a spherical optical power.

8. The optical device according to claim 1, wherein the computer executable instructions comprise instructions for adjusting the prism of the active programmable lens.

9. The optical device according to claim 1, wherein the memory is adapted to store a plurality of predetermined optical power states, each predetermined optical power state corresponding to an optical power relative to a range of vision distance and/or vision direction of said at least one eye of the wearer.

10. The optical device according to claim 1, wherein the active programmable lens is a Fresnel lens and wherein the computer executable instructions comprise instructions for adjusting at least one prismatic optical power from one predetermined optical power state to another so as to move a central ring upon the vision direction of said at least one eye of the wearer.

11. The optical device according to claim 1, wherein the at least two predetermined optical power states comprise a non-uniform and progressive spherical optical power distribution, and wherein a geometrical variation of optical power of the active programmable lens is smaller than or equal to 1 D.

12. The optical device according to claim 1, further comprising at least two active programmable optical lenses having adjustable optical powers and extending respectively between right and left eyes of the wearer and the real world scene when the optical device is worn by the wearer, and wherein the computer executable instructions comprise instructions for adjusting the optical power of both active programmable optical lenses.

13. The optical device according to claim 1, wherein the adjustment resolution of the adjustable optical power of the active programmable lens is larger than or equal to 0.1 D.

14. The optical device according to claim 1, wherein the vision sensor is adapted to measure a vision direction of said at least one eye of the wearer and wherein the computer executable instructions comprise instructions for adjusting an optical power and/or an optical center, of the active programmable lens based on the vision direction of said at least one eye of the wearer.

15. The optical device according to claim 1, wherein the memory is adapted to store at least four predetermined optical power states, each predetermined optical power state corresponding to an optical power relative to a range of vision distance and/or vision direction of the at least one eye of the wearer.

16. The optical device according claim 1, wherein the vision sensor is adapted to measure a vision direction of said at least one eye of the wearer and wherein the computer executable instructions comprise instructions for adjusting an optical function of the active programmable lens based on the vision direction of said at least one eye of the wearer.

17. The optical device according to claim 16, wherein the computer executable instructions comprise instructions for moving the optical function of the active programmable lens with the vision direction of said at least one eye of the wearer.

\* \* \* \* \*